United States Patent
Kiani et al.

(10) Patent No.: US 9,364,181 B2
(45) Date of Patent: Jun. 14, 2016

(54) PHYSIOLOGICAL SENSOR COMBINATION

(75) Inventors: Massi E. Kiani, Laguna Niguel, CA (US); Ammar Al-Ali, Tustin, CA (US); Ronald Coverston, Portola Hills, CA (US); Gene Mason, La Habra Heights, CA (US); Fred Robertson, Mequon, WI (US)

(73) Assignee: Masimo Corporation, Irvine, CA (US)

( * ) Notice: Subject to any disclaimer, the term of this patent is extended or adjusted under 35 U.S.C. 154(b) by 103 days.

(21) Appl. No.: 11/210,128

(22) Filed: Aug. 23, 2005

(65) Prior Publication Data

US 2005/0277819 A1 Dec. 15, 2005

Related U.S. Application Data

(63) Continuation of application No. 10/325,699, filed on Dec. 19, 2002, now Pat. No. 6,934,570.

(60) Provisional application No. 60/347,047, filed on Jan. 8, 2002.

(51) Int. Cl.
  *A61B 5/0478* (2006.01)
  *A61B 5/145* (2006.01)
  *A61B 5/00* (2006.01)
  *A61B 5/1455* (2006.01)

(52) U.S. Cl.
  CPC .............. *A61B 5/6814* (2013.01); *A61B 5/0478* (2013.01); *A61B 5/14552* (2013.01); *A61B 2562/164* (2013.01)

(58) Field of Classification Search
  CPC ........... A61B 2562/164; A61B 5/0478; A61B 5/14552; A61B 5/6814

USPC ......... 600/323, 324, 326, 300, 301, 481, 529, 600/483–485, 500–503, 536, 538, 508, 509, 600/544, 545, 372, 386, 391, 393, 382–384

See application file for complete search history.

(56) References Cited

U.S. PATENT DOCUMENTS

| | | |
|---|---|---|
| 4,854,699 A | 8/1989 | Edgar, Jr. |
| 4,865,038 A | 9/1989 | Rich et al. |
| 4,942,877 A * | 7/1990 | Sakai et al. .................... 600/323 |
| 4,955,380 A | 9/1990 | Edel |
| 4,957,109 A | 9/1990 | Groeger et al. |
| 4,960,128 A | 10/1990 | Gordon et al. |
| 4,964,408 A | 10/1990 | Hink et al. |
| 5,163,438 A | 11/1992 | Gordon et al. |
| 5,337,744 A | 8/1994 | Branigan |
| 5,431,170 A | 7/1995 | Mathews |
| 5,452,717 A | 9/1995 | Branigan et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,584,296 A | 12/1996 | Cui et al. |

(Continued)

*Primary Examiner* — Navin Natnithithadha (74) *Attorney, Agent, or Firm* — Knobbe Martens Olson & Bear LLP (57) ABSTRACT

A physiological sensor combination has a flexible substrate configured to attach to a tissue site. Multiple sensors are disposed on the substrate, which generate physiological signals. Each of the signals is responsive to a different physiological parameter. Conductors are carried on the substrate and routed between the sensors and at least one connector. The connector is configured to communicate the physiological signals to at least one monitor, which derives measurements of the parameters.

4 Claims, 7 Drawing Sheets

(56) References Cited

U.S. PATENT DOCUMENTS

| | | | |
|---|---|---|---|
| 5,590,649 A | 1/1997 | Caro et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,678,544 A * | 10/1997 | DeLonzor et al. | 600/344 |
| 5,685,299 A | 11/1997 | Diab et al. | |
| 5,697,367 A | 12/1997 | Lewis et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,795,292 A * | 8/1998 | Lewis et al. | 600/323 |
| 5,810,734 A | 9/1998 | Caro et al. | |
| 5,817,008 A * | 10/1998 | Rafert et al. | 600/323 |
| 5,823,950 A | 10/1998 | Diab et al. | |
| 5,830,131 A | 11/1998 | Caro et al. | |
| 5,833,618 A | 11/1998 | Caro et al. | |
| 5,839,439 A | 11/1998 | Nierlich et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,032,065 A * | 2/2000 | Brown | 600/383 |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,112,107 A * | 8/2000 | Hannula | 600/310 |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,171,258 B1 | 1/2001 | Karakasoglu et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,298,255 B1 | 10/2001 | Cordero et al. | |
| 6,315,719 B1 * | 11/2001 | Rode et al. | 600/300 |
| 6,334,065 B1 | 12/2001 | Al-Ali et al. | |
| 6,349,228 B1 | 2/2002 | Kiani et al. | |
| 6,358,212 B1 * | 3/2002 | Hasegawa et al. | 600/485 |
| 6,360,114 B1 | 3/2002 | Diab et al. | |
| 6,371,921 B1 | 4/2002 | Caro et al. | |
| 6,377,829 B1 | 4/2002 | Al-Ali | |
| 6,385,473 B1 * | 5/2002 | Haines et al. | 600/393 |
| 6,388,240 B2 | 5/2002 | Schulz et al. | |
| 6,397,091 B2 | 5/2002 | Diab et al. | |
| 6,416,471 B1 * | 7/2002 | Kumar et al. | 600/300 |
| 6,430,525 B1 | 8/2002 | Weber et al. | |
| 6,454,708 B1 * | 9/2002 | Ferguson et al. | 600/300 |
| 6,463,311 B1 | 10/2002 | Diab | |
| 6,470,199 B1 | 10/2002 | Kopotic et al. | |
| 6,494,829 B1 * | 12/2002 | New et al. | 600/300 |
| 6,501,975 B2 | 12/2002 | Diab et al. | |
| 6,515,273 B2 | 2/2003 | Al-Ali | |
| 6,519,484 B1 * | 2/2003 | Lovejoy et al. | 600/323 |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Diab et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,694,160 B2 * | 2/2004 | Chin | 600/344 |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,725,075 B2 | 4/2004 | Al-Ali | |
| 6,745,060 B2 | 6/2004 | Diab et al. | |
| 6,760,607 B2 | 7/2004 | Al-All | |
| 6,763,256 B2 * | 7/2004 | Kimball et al. | 600/336 |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,879,850 B2 * | 4/2005 | Kimball | 600/336 |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 * | 8/2005 | Kiani et al. | 600/324 |
| 7,496,400 B2 * | 2/2009 | Hoskonen et al. | 600/544 |
| 2003/0225323 A1 * | 12/2003 | Kiani et al. | 600/323 |
| 2004/0030258 A1 * | 2/2004 | Williams et al. | 600/544 |
| 2005/0096513 A1 * | 5/2005 | Ozguz et al. | 600/301 |

\* cited by examiner

PHYSIOLOGICAL SENSOR COMBINATION

CROSS-REFERENCE TO RELATED APPLICATIONS

This application claims priority benefit under 35 U.S.C. §120 from, and is a continuation of U.S. patent application Ser. No. 10/325,699, filed Dec. 19, 2002, entitled "Physiological Sensor Combination," now U.S. Pat. No. 6,934,570, which claims priority benefit under 35 U.S.C. §119(e) from U.S. Provisional Patent Application No. 60/347,047, filed Jan. 8, 2002, entitled "Physiological Sensor Combination." The present application incorporates the foregoing disclosures herein by reference.

BACKGROUND OF THE INVENTION

Pulse oximetry is a widely accepted noninvasive procedure for measuring the oxygen saturation level of arterial blood, an indicator of a person's oxygen supply. Early detection of low blood oxygen level is important in the medical field, for example in critical care and surgical applications, because an insufficient supply of oxygen can result in brain damage and death in a matter of minutes. A pulse oximetry system consists of a sensor applied to a patient, a pulse oximeter, and a patient cable connecting the sensor and the pulse oximeter. The pulse oximeter typically provides a numerical readout of the patient's oxygen saturation, a numerical readout of pulse rate, and an audible indication of each pulse. In addition, the pulse oximeter may display the patient's plethysmograph, which provides a visual indication of the patient's pulse contour and pulse rate.

Measuring a biopotential signal, such as an electroencephalogram (EEG) is also a widely accepted procedure for patient monitoring and diagnostic tests. An EEG measures cortical activity of the brain, which can reflect changes in cortical or subcortical cellular function due to insufficient oxygen or drugs, to name a few. For example, changes in EEG bandwidth and power can provide a measure of the effects of anesthetics on the brain. A biopotential measurement system consists of a bipotential sensor, a monitor and a patient cable connecting the sensor to the monitor. For example, an EEG monitor measures the potential difference between at least two well-spaced electrodes, using a separate ground electrode, and displays the resulting signal.

SUMMARY OF THE INVENTION

A physiological sensor combination has a flexible substrate configured to attach to a tissue site. Multiple sensors are disposed on the substrate, which generate physiological signals. Each of the signals is responsive to a different physiological parameter. Conductors are carried on the substrate and routed between the sensors and at least one connector. The connector is configured to communicate the physiological signals to at least one monitor, which derives measurements of the parameters. In one embodiment, the sensors comprise multiple electrodes disposed on the substrate. Each of the electrodes is adapted to be in electrical communication with the tissue site and electrically connect to at least one of the conductors. Further, an emitter and a detector are mounted to the substrate and electrically connected to at least one of the conductors. The emitter is adapted to transmit light into the tissue site, and the detector is adapted to receive reflected light from the tissue site.

In a particular embodiment, the substrate has a first side adapted to face toward the tissue site and a second side adapted to face away from the tissue site, where the conductors and the electrodes are disposed on the first side and the emitter and the detector are mounted to the first side. The substrate may comprise a fold-over portion having a circuit side corresponding to the first side, where the fold-over portion is adapted to fold so that the circuit side is proximate the second side. Further, the emitter and the detector may be mounted to the fold-over portion. The substrate may define at least one aperture configured so that the emitter and the detector each align with a corresponding aperture when the fold-over is in a folded position.

In another particular embodiment, the physiological sensor combination comprises a plurality of biopotential sensor pinouts corresponding to the electrodes, a plurality of optical sensor pinouts corresponding to the emitter and the detector, and a common connector extending from the substrate. The biopotential sensor pinouts and said optical sensor pinouts are each disposed on the common connector.

Another aspect of a physiological sensor combination is a substrate means for combining a first sensor and a second sensor, a connector means for communicating signals from the first sensor and the second sensor to at least one monitor, and an identifying means of conveying information about each of the first sensor and the second sensor to the monitor. The physiological sensor combination may further comprise a fold-over means for positioning sensor components so as to extend away from a tissue site. The physiological sensor combination may additionally comprise an aperture means for providing light communications between sensor components and the tissue site.

DETAILED DESCRIPTION OF THE PREFERRED EMBODIMENTS

Figure 1:
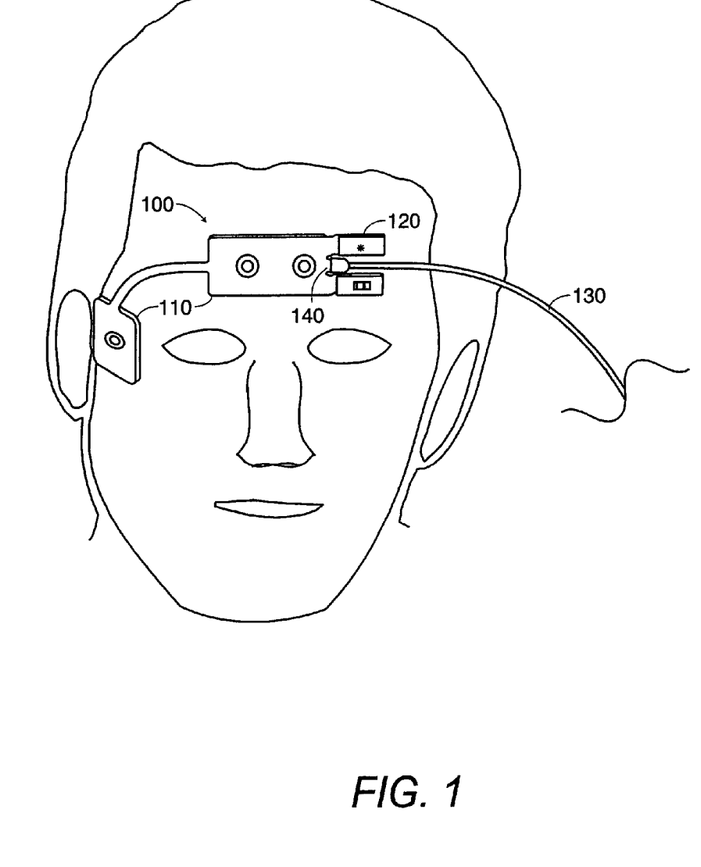
FIG. 1 is an illustration of a physiological sensor combination applied to a patient and having a patient cable connected near the patient's forehead.
Figure 2:
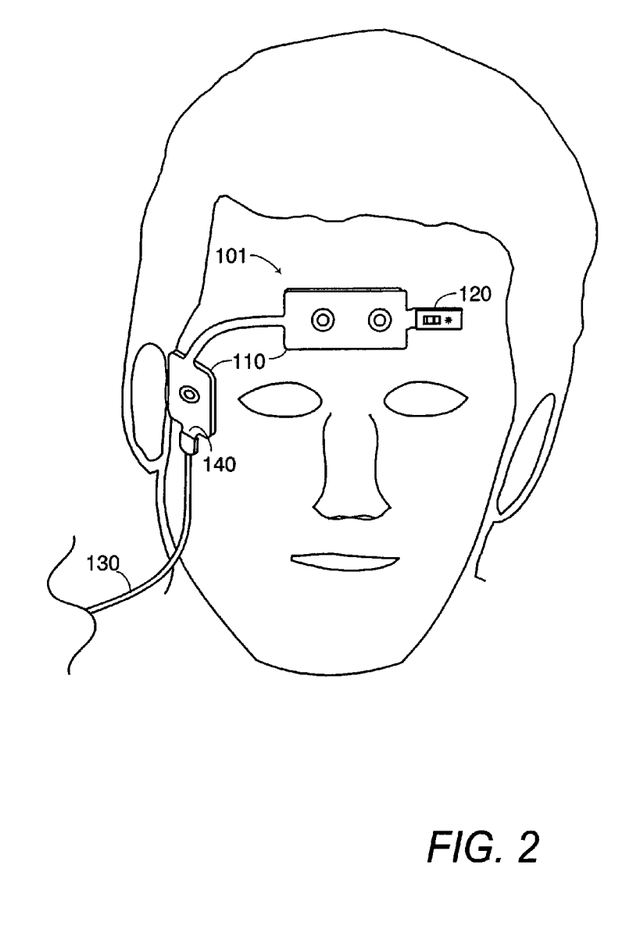
FIG. 2 is an illustration of a physiological sensor combination applied to a patient and having a patient cable connected near the patient's temple.
Figure 3A:
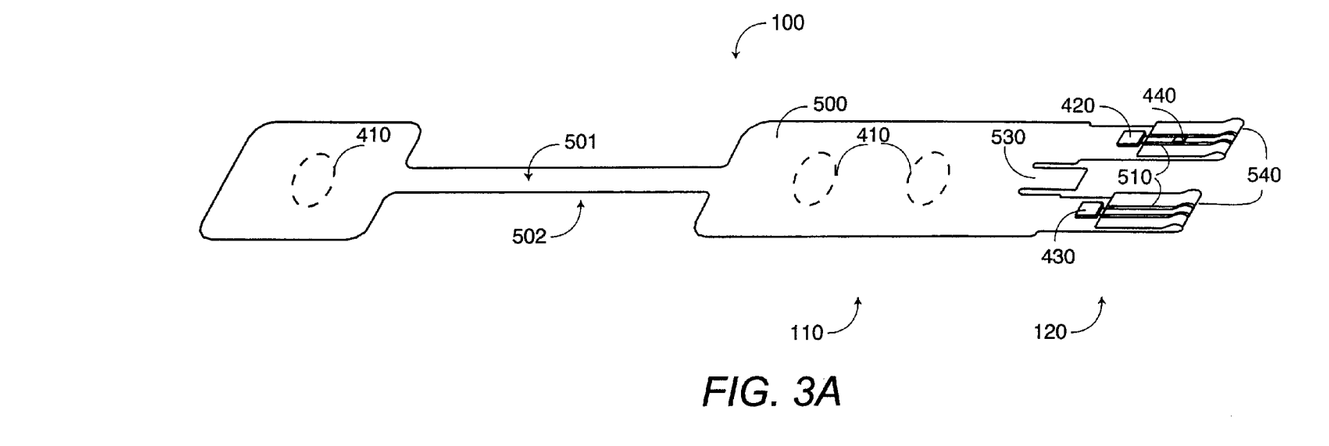
FIGS. 3A-B are perspective views of a circuit substrate and an assembled sensor, respectively, for a physiological sensor combination having a single-sided circuit substrate and a shared connector.
Figure 3B:
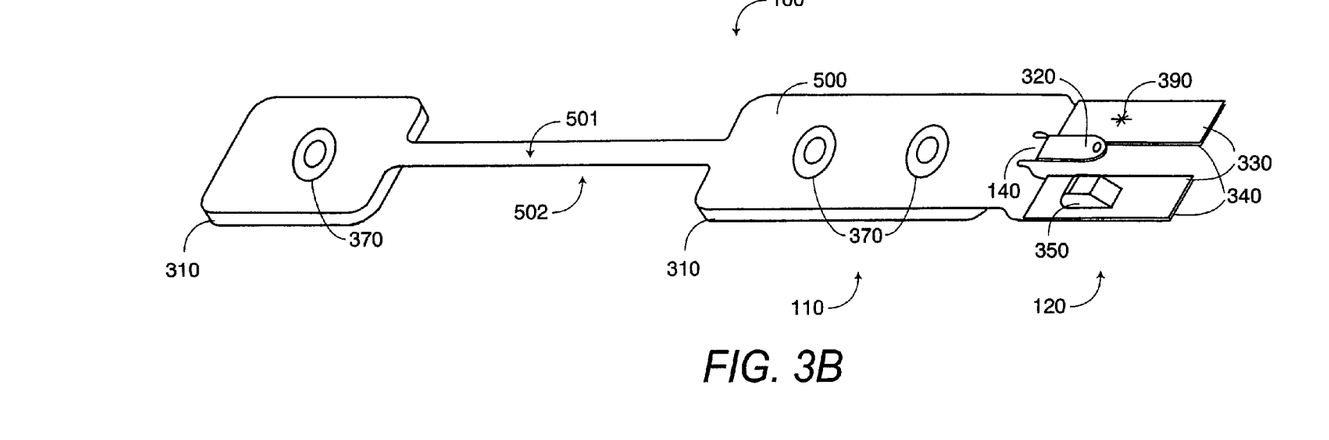
Figure 4:
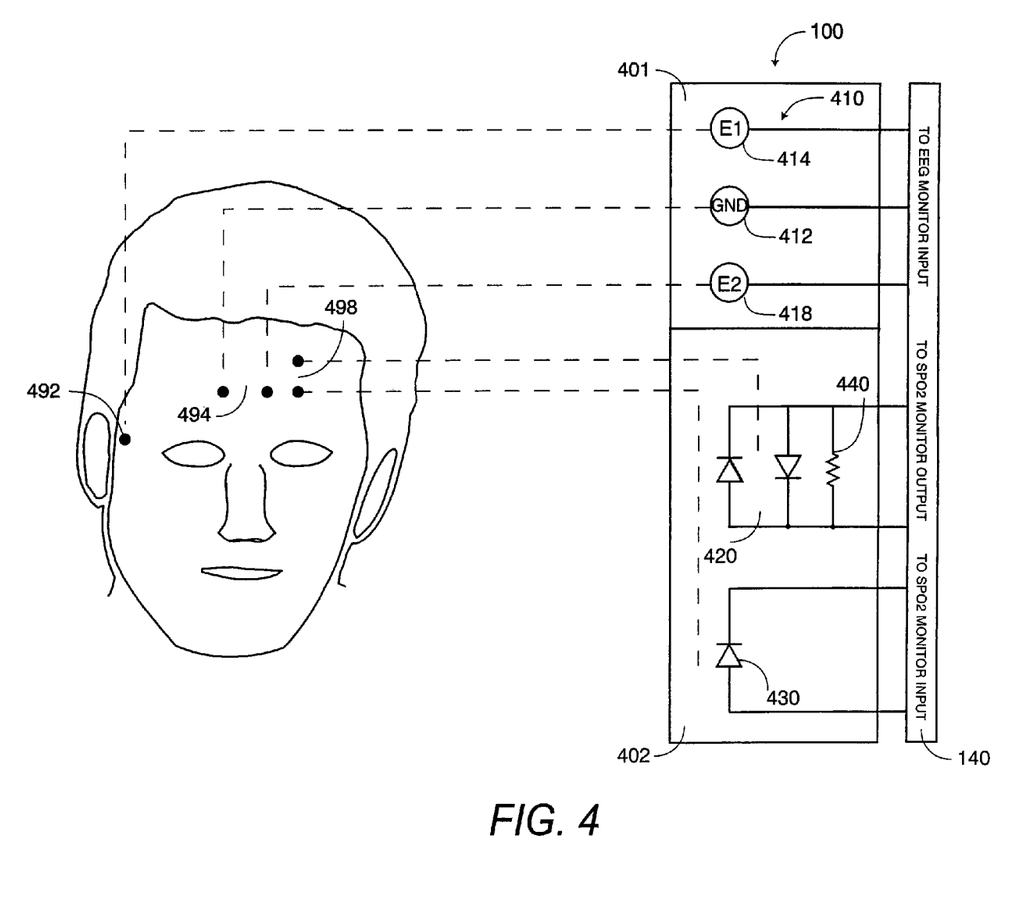
FIG. 4 is a schematic diagram of a physiological sensor combination showing the location of applied sensor components.
Figure 5:
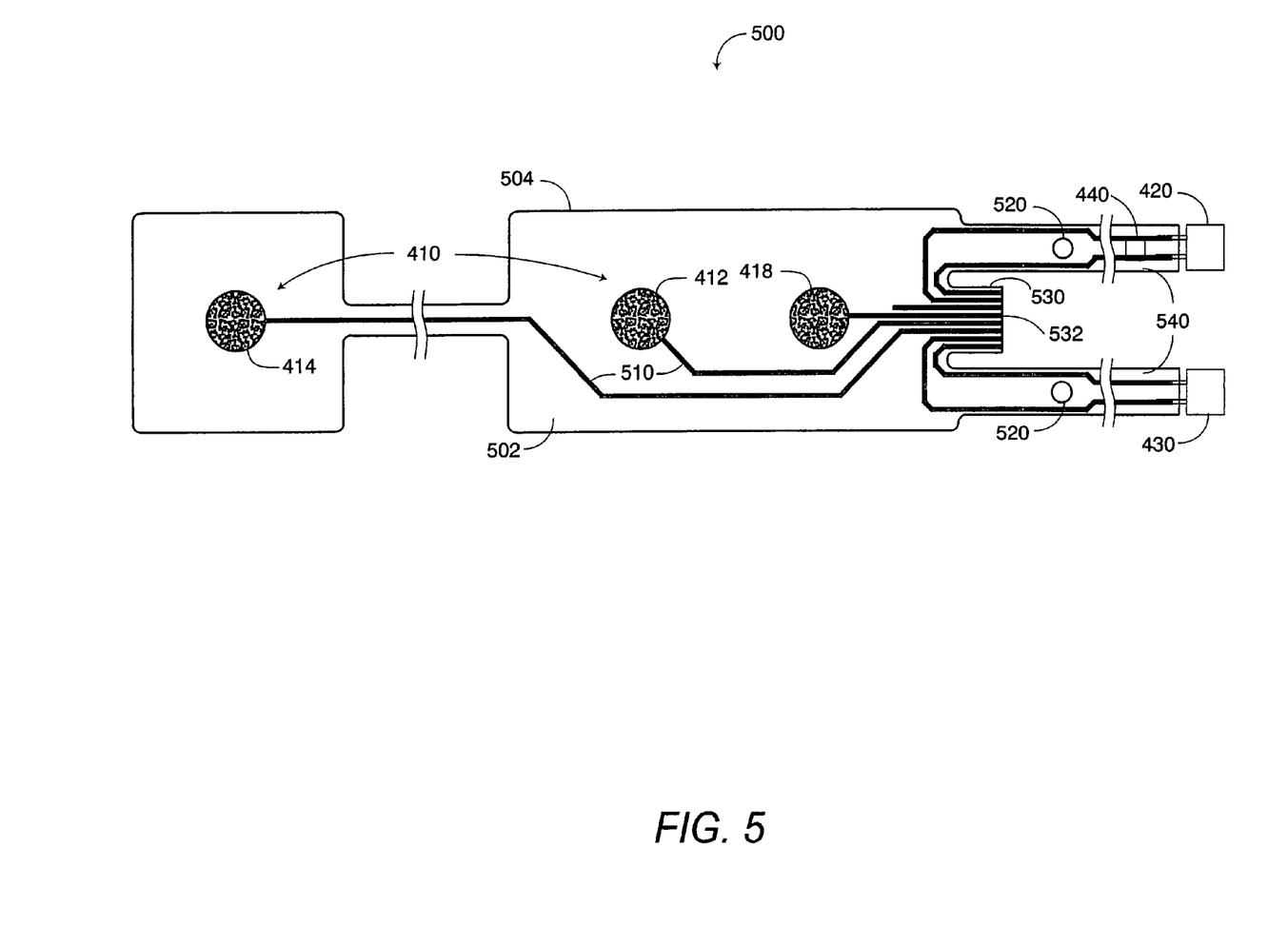
FIG. 5 is a layout diagram of a single-sided circuit for a physiological sensor combination.
Figure 6:
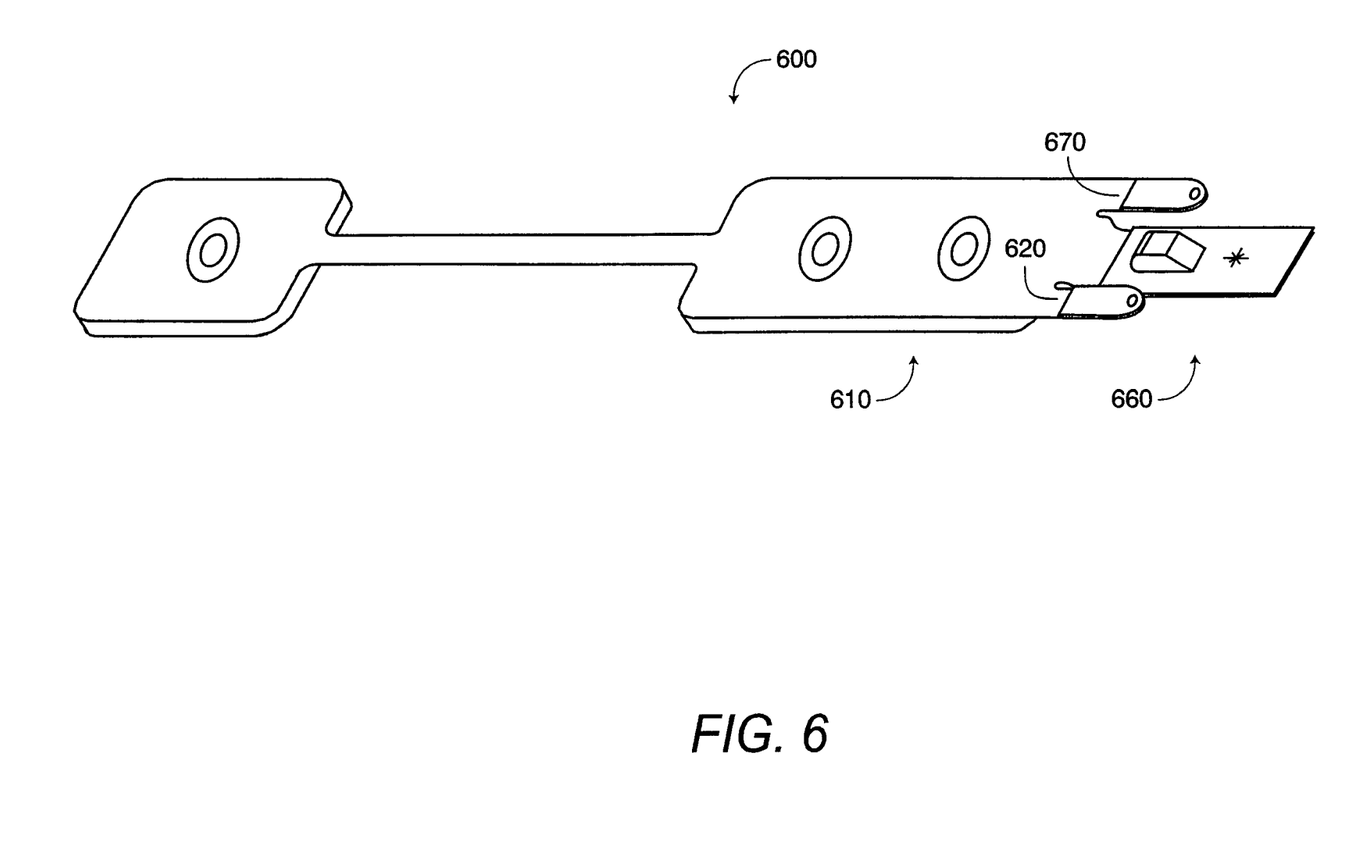
FIG. 6 is a perspective view of a physiological sensor combination having a single-sided circuit substrate and dual connectors.
Figure 7:
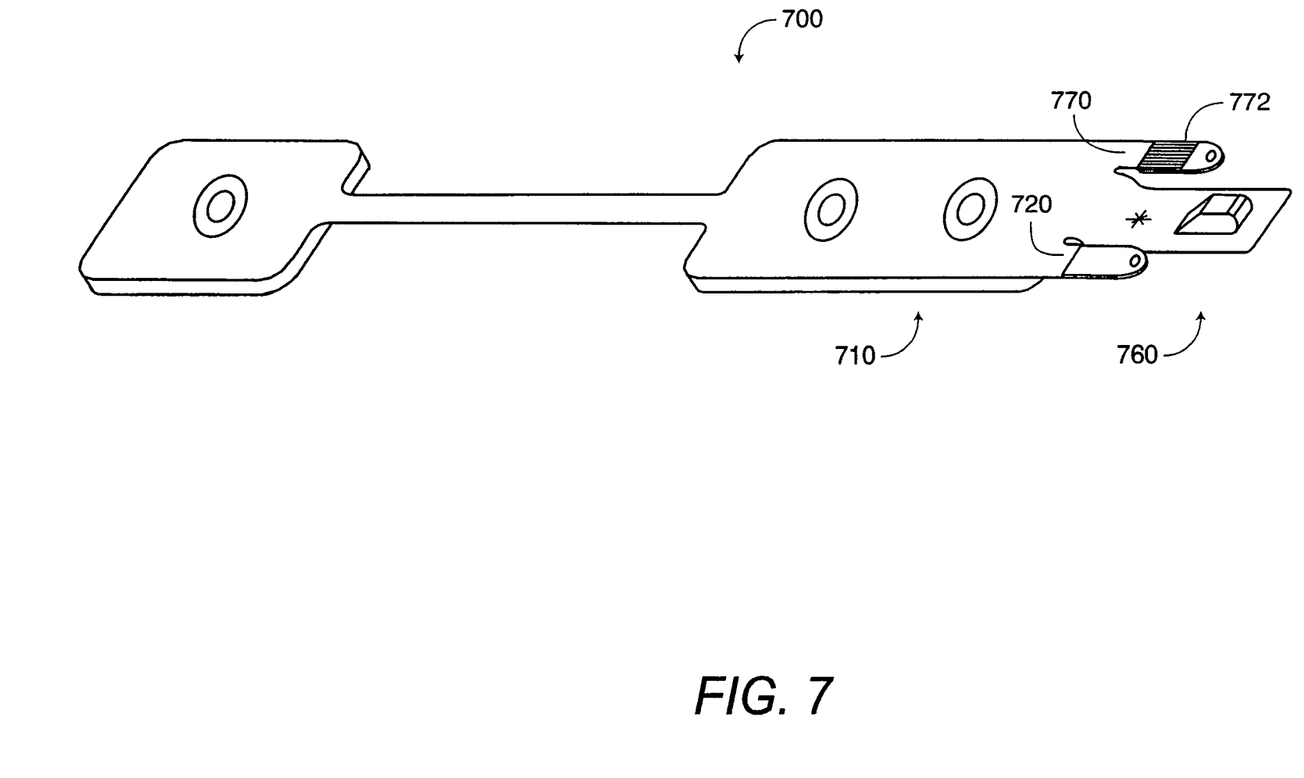
FIG. 7 is a perspective view of a physiological sensor combination having a double-sided circuit substrate and dual connectors.

FIGS. 1-2 show a physiological sensor combination applied to a patient. FIGS. 3-5 illustrate a physiological sensor combination having a biopotential sensor and an optical sensor configured on a single-sided flexible circuit substrate with a shared patient cable connector. FIG. 6 illustrates a physiological sensor combination also having a biopotential sensor and an optical sensor configured on a single-sided flexible circuit substrate. The biopotential sensor and the optical sensor, however, each have separate patient cable connectors. FIG. 7 illustrates a physiological sensor combination having a biopotential sensor and an optical sensor configured on a double-sided circuit substrate, each sensor also having separate patient cable connectors.

FIGS. 1-2 illustrate a physiological sensor combination applied to the forehead and temple areas of a patient. A patient cable 130 connects the physiological sensor combination 100 (FIG. 1), 101 (FIG. 2) to one or more monitoring devices (not shown). As shown in FIG. 1, the patient cable 130 may connect near the patient's forehead. As shown in FIG. 2, the patient cable 130 may alternatively connect near the patient's temple. The biopotential sensor 110 and optical sensor 120 may share a common connector 140. Alternatively, the biopotential sensor 110 and optical sensor 120 may each have a dedicated patient cable connector, as described in further detail with respect to FIGS. 6-7, below. The biopotential sensor 110 may be an EEG sensor for depth of consciousness monitoring, as described above. The optical sensor 120 may be a pulse oximetry reflectance sensor for oxygen saturation monitoring, also described above FIGS. 3A-B illustrate a physiological sensor combination 100 having a biopotential sensor 110 and an optical sensor 120 configured on a flexible circuit substrate 500. As shown in FIG. 3A, the flexible circuit 500 is single-sided, having a blank side 501 and a circuit side 502 with printed conductive traces 510 on the circuit side 502. The biopotential sensor 110 has electrodes 410 (not visible and shown as dashed lines) printed on the circuit side 502. The electrodes 410 are configured so that one electrode is applied to the temple area and two electrodes are applied to the forehead, as further described with respect to FIGS. 4-5, below.

Further shown in FIG. 3A, the optical sensor 120 includes a fold-over 540, an emitter 420, a detector 430 and an information element 440. The emitter 420, detector 430 and information element 440 are each mounted to the circuit side 502 on the fold-over 540 and electrically connected to traces 510, as described in detail with respect to FIGS. 4-5, below. The optical sensor 120 is configured so that emitter 420 and a detector 430 are applied over the forehead, also described with respect to FIGS. 4-5, below. The fold-over 540 is such that each of the emitter 420 and detector 430 align with corresponding apertures 520 (FIG. 5) so that light transmitted from the emitter 420 passes through an aperture 520 (FIG. 5) and into a patient's skin and that reflected light passes out of a patient's skin, through an aperture 520 (FIG. 5) and is received by the detector 430. The substrate 500 has a stub 530 that contains pinouts 532 (FIG. 5), which connect to the electrodes 410 and also to the emitter 420, detector 430 and information element 440, also described in detail with respect to FIGS. 4-5, below. Emitters and a detector for a pulse oximetry sensor are described in detail in U.S. Pat. No. 6,256,523 entitled "Low Noise Optical Probe," which is assigned to Masimo Corporation and incorporated by reference herein. An information element for a pulse oximetry sensor is described in detail in U.S. Pat. No. 6,011,986 entitled "Manual And Automatic Probe Calibration," which is assigned to Masimo Corporation and incorporated by reference herein.

As shown in FIG. 3B, the biopotential sensor 110 has an adhesive foam layer 310 disposed around the electrodes 410 on the circuit side 502. The foam layer 310 has an adhesive for patient skin attachment and cushions the biopotential sensor 110 against the skin. Further, the foam layer 310 forms cavities around the electrodes 410 that are filled with a conductive gel for electrical communication between a tissue site and the electrodes 410. Printed electrode indicators 370 facilitate sensor application on a tissue site. Electrodes printed on a substrate, an associated foam layer, and gel-filled foam cavities are described in detail in U.S. Pat. No. 6,032,064 entitled "Electrode Array System For Measuring Electrophysiological Signals," assigned to Aspect Medical Systems, Inc. and incorporated by reference herein. One of ordinary skill in the art will recognize that various electrode configurations may be utilized as the biopotential sensor 110.

Also shown in FIG. 3B, the optical sensor 120 has a face tape 330 and a base tape 340 that envelop the fold-over 540 along with the fold-over mounted components 420-440. In one embodiment, the face tape 330 and base tape 340 attach together and to the fold-over 540 with PSA. Further, the base tape 340 has a backing (not shown) that is removed to expose an adhesive for skin attachment. The face tape 330 also secures the detector 430 within an optical cavity and cover 350. A printed emitter indicator 390 facilitates sensor application on a tissue site. Emitters, detectors, optical cavities and corresponding covers are described in detail in U.S. Pat. No. 6,256,523, referenced above.

Further shown in FIG. 3B, the physiological sensor combination 100 has a tab 320 that attaches to the stub 530 (FIG. 3A) to complete the connector 140. In one embodiment, the attachment is accomplished with pressure sensitive adhesive (PSA) between the tab 320 and stub 530. The tab 320 provides a stiffener for the pinouts 532 (FIG. 5) and an insertion and locking mechanism for a mating patient cable connector, as described in U.S. Pat. No. 6,152,754 entitled "Circuit Board Based Cable Connector" and U.S. Pat. No. 6,280,213 entitled "Patient Cable Connector," each assigned to Masimo Corporation and incorporated by reference herein.

The physiological sensor combination 100 is described above with respect to a fold-over that positions the optical sensor components 420-440 so that they extend away from the tissue site. This advantageously allows a smooth surface to be positioned against the tissue site for patient comfort. In another embodiment, however, there is no fold-over 540 and the components 420-440 extend from the substrate toward the tissue site. In yet another embodiment, there is no fold-over and the components 420 are mounted on the substrate side opposite the conductors and utilize substrate feed-throughs to connect with the flex circuit traces 510. Further, the fold-over 540 is described above as positioning the emitter 420 and detector 430 over substrate apertures 520 (FIG. 5). In an alternative embodiment, the fold-over 540 is skewed so that the emitter 420 and detector 430 are positioned away from the substrate so that no apertures are necessary.

FIG. 4 illustrates a circuit diagram for a physiological sensor combination 100 having a biopotential sensor circuit 401 and an optical sensor circuit 402. The biopotential sensor circuit 401 has an electrode array 410, which is placed on well-separated skin areas. In one embodiment, a first electrode 414 is placed on a temple area 492 and a second electrode 418 is placed on a forehead area 494. A ground electrode 412 is also placed on the forehead area 494 near the second electrode 418. Each electrode of the array 410 provides a pinout to a connector 140. The connector 140 provides sensor input to a monitor. The electrodes placed on the patient's head transmit EEG signals to a monitor, which may include a separate digitizer located near the patient to reduce electrical noise. The difference in potential between the first electrode 414 and second electrode 418 reflects primarily a far-field electrical source, i.e. the EEG from the distant brain cortex, and not a near-field electrical source, such as transdermal nervous stimulation of muscle. The monitor filters the EEG data, analyzes it for artifact and extracts characteristic features from the complex signal to provide pattern recognition of changes over time.

Also shown in FIG. 4, the optical sensor circuit 402 has an emitter 420, a detector 430 and an information element 440. The emitter 420 includes both a red LED (light emitting diode) and an infrared (IR) LED in a back-to-back arrangement. In alternative embodiments, the red and IR LEDs are arranged in three-wire, common anode or common cathode configurations, as is well-known in the art. The detector 430 is a photodiode. The LEDs 420 and photodiode 430 are located on the skin in close proximity, such as on a forehead area 498. In this manner, the LEDs emit light into the blood vessels and capillaries underneath the skin, and the photodiode 430 is positioned to detect the LED emitted light reflected from the skin tissues. The emitter 420 and detector 430 provide pinouts to the connector 140, which provides a sensor input to a monitor. The monitor determines oxygen saturation by computing the differential absorption by arterial blood of the two wavelengths of light projected into the skin from the emitter 420, as is well-known in the art. The monitor provides LED drive current, which alternately activates the red and IR LEDs. The detector 430 uses a single photodiode that responds to both the red and infrared emitted light and generates a time-division-multiplexed ("modulated") output signal to the monitor, corresponding to the red and infrared light energy attenuated by absorption and reflection from the patient's tissue. The monitor has front-end circuitry for amplification, filtering and digitization of the detector signal. The monitor also has a signal processor that calculates a ratio of detected red and infrared intensities, and an arterial oxygen saturation value is empirically determined based on that ratio.

Further shown in FIG. 4, the optical sensor circuit 402 may have an information element 440, such as a resistor configured in parallel with the emitter 420 LEDs. The information element 440 can be read by the monitor and used to determine such things as LED wavelength, sensor type or manufacturer. Information elements and monitor reading of information elements are described in U.S. Pat. No. 6,011,986, referenced above. Advantageously, although associated with the optical sensor circuit 402, the information element 440 can be used to designate information regarding the biopotential sensor portion of the physiological sensor combination 100. For example, the information element 440 can specify the number of electrodes as well as the electrode locations on the head.

FIG. 5 illustrates a flexible circuit 500 for a physiological sensor combination 100. The flexible circuit 500 has a substrate 504, traces 510, electrodes 410, pinouts 530 and apertures 520. Conductors are deposited and/or etched on a circuit side 502 of the substrate 504 in a pattern to form the traces 510, electrodes 410 and pinouts .532, as is well known in the art. In one embodiment, the substrate 504 is a flexible polyester film and the conductors are silver/silver-chloride. In another embodiment, the conductors are copper. The components 420-440 attach to the flexible circuit 500 and are electrically connected to the traces 510, such as with solder. The fold-over 540 is configured so that the emitter 420 and detector 430 align with the corresponding apertures 520.

FIG. 6 illustrates a physiological sensor combination 600 having a biopotential sensor 610 and an optical sensor 660. The biopotential sensor 610 is configured as described with respect to FIGS. 3-5, above, except that the physiological sensor combination 600 has a connector 620 that is dedicated to the biopotential sensor 610 rather than being shared with the optical sensor 660. The optical sensor 660 also is configured as described with respect to FIGS. 3-5, above, except that a connector 670 is dedicated to the optical sensor 660 rather than being shared with the biopotential sensor 610. Further, the optical sensor 660 has a single fold-over (not visible) on which is mounted the emitter 420 (FIG. 4) and detector 430 (FIG. 4) rather than having a separate fold-over 540 (FIG. 3A) for each.

FIG. 7 illustrates a physiological sensor combination 700 having a biopotential sensor 710 and an optical sensor 760. The biopotential sensor 710 is configured as described with respect to FIG. 6, above. The optical sensor 760 also is configured as described with respect to FIG. 6, above, except that the flexible circuit 500 (FIG. 5) is double-sided, i.e. the traces 510 (FIG. 5) associated with the biopotential sensor 710 are on the side facing the patient's skin when applied, and the traces 510 (FIG. 5) associated with the optical sensor 760 are on the side away from the patient's skin when applied. As a result, the connector 770 is dedicated to the optical sensor 760 and has pinouts 772 facing away from the patient's skin when applied. Further, the optical sensor 760 does not have a fold-over 540 (FIG. 3A). Rather, the optical sensor components 420-440 (FIG. 4) are mounted on the flexible circuit side away from the patient's skin.

A physiological sensor combination is described above with either a shared patient cable connector or a patient cable connector dedicated to each sensor. One of ordinary skill will recognize that either connector configuration will allow the sensor to communicate with a single monitor that analyzes and displays multiple physiological parameters or, alternatively, multiple monitors that are dedicated to analyzing only related physiological parameters, such as oxygen saturation and pulse rate.

The physiological sensor combination as described above can be cost effectively manufactured, advantageously allowing disposable use. One of ordinary skill in the art will recognize that, however, that the physiological sensor combination as disclosed herein can be similarly applied to construct a reusable sensor combination.

The physiological sensor combination was also described above with respect to a shared substrate. One of ordinary skill in the art will recognize that a physiological sensor combination can be constructed from, for example, a biopotential sensor configured on a first substrate and an optical sensor configured on a second substrate, where the first substrate and the second substrate are joined together during the manufacturing process to form a multilayer substrate or an otherwise integrated substrate incorporating multiple sensors.

Although a physiological sensor combination is described above with respect to a biopotential sensor combined with an optical sensor applied to a patient's head, one of ordinary skill in the art will recognize that a physiological sensor combination may be applied to other tissue sites and utilize other sensor combinations, where there is a need to combine two or more sensors in one to accommodate sensors competing for the same tissue site. For example, a physiological sensor combination may include a noninvasive blood pressure (NIBP) sensor and a pulse oximetry sensor or a NIBP sensor and a respiration rate sensor for monitoring on the forearm or the wrist. As another example, a physiological sensor combination may include two optical sensors and one biopotential sensor applied to the forehead and configured as a pulse oximetry sensor and a EEG sensor, as described above, in addition to a near infrared spectroscopy sensor for measuring cerebral tissue oxygenation.

A biopotential sensor as described above could be used in conjunction with a depth of anesthesia monitor that uses not just passive EEG, but also active EEG. That is an Evoked Potential EEG can be used, where some kind of sound is played and changes in EEG are observed as the patient goes into consciousness.

A physiological sensor combination has been disclosed in detail in connection with various embodiments. These embodiments are disclosed by way of examples only and are not to limit the scope of the claims that follow. One of ordinary skill in the art will appreciate many variations and modifications.

What is claimed is:

1. A forehead sensor configured to output signals responsive to physiological parameters of a wearer thereof, the forehead sensor comprising:
   a reflectance-type oximetry sensor including a light source and at least one light detector configured to output a signal responsive to attenuation of reflected light from said light source;
   at least one electrode pair including a first and second electrode; and
   an attachment mechanism, said attachment mechanism configured to be worn on a front of a forehead of a wearer and position the light source and detector in a first measurement area on the forehead, and position the electrode pair in a second measurement area on the forehead, said first measurement area not divided by said second measurement area between said position of said light source and said position of said detector, said oximetry sensor configured to monitor said first measurement area and said electrode pair configured to monitor said second measurement area.

2. The forehead sensor of claim 1, comprising an information element in parallel with said light source and accessible by a physiological monitor, said information element adapted to provide said physiological monitor information about said forehead sensor electronics.

3. The forehead sensor of claim 1, comprising a plurality of conductors eventually grouped in a single connector, wherein said connector is configured to communicate at least said signal to a physiological monitor.

4. A sensor adapted to a forehead of a patient, the sensor including an optical sensor and an electrode sensor, the sensor comprising:
   the optical sensor configured to output an optical sensor signal responsive to attenuation of reflected light from said light source, said attenuation caused by tissue at a first measurement site;
   the electrode sensor including at least one electrode pair, the electrode sensor configured to output an electrode sensor signal responsive to electrical signals at a second measurement site; and
   adhesive attachment tape including one or more portions, the tape configured to be worn on a forehead of the patient and position the optical sensor and the electrode sensor, wherein said first measurement site is not divided by said second measurement site between said position of said optical sensor and said position of said electrode sensor.

* * * * *